(12) United States Patent
Brun

(10) Patent No.: US 10,390,911 B2
(45) Date of Patent: *Aug. 27, 2019

(54) ABUTMENT POSITION LOCATOR

(71) Applicant: Nobel Biocare Services AG, Zurich-Flughafen (CH)

(72) Inventor: Philipp Brun, Basel (CH)

(73) Assignee: Nobel Biocare Services AG, Kloten (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/245,928

(22) Filed: Aug. 24, 2016

(65) Prior Publication Data

US 2016/0374783 A1  Dec. 29, 2016

Related U.S. Application Data

(63) Continuation of application No. 14/271,268, filed on May 6, 2014, now Pat. No. 9,468,506, which is a continuation of application No. 13/341,328, filed on Dec. 30, 2011, now Pat. No. 8,747,112.

(51) Int. Cl.
*A61C 8/00* (2006.01)

(52) U.S. Cl.
CPC .......... *A61C 8/0089* (2013.01); *A61C 8/0001* (2013.01); *A61C 8/0028* (2013.01); *A61C 8/0057* (2013.01); *A61C 8/0062* (2013.01); *A61C 8/0066* (2013.01); *A61C 2008/0084* (2013.01)

(58) Field of Classification Search
CPC ..... A61C 8/0001; A61C 8/0022; A61C 8/005; A61C 8/0033; A61C 8/0066; A61C 8/0028; A61C 8/0057; A61C 8/0062; A61C 13/12; A61C 13/2656; A61C 7/14; A61C 2008/0084
USPC .......... 433/172–174, 177, 191, 213–214, 75; 285/120.1, 120.4, 137, 239, 123.14, 285/123.9, 124.4; 606/264, 265, 300, 606/301, 315, 217, 59, 331
See application file for complete search history.

(56) References Cited

U.S. PATENT DOCUMENTS

| | | |
|---|---|---|
| 3,328,879 A | 7/1967 | Bax |
| 3,787,975 A | 1/1974 | Zuest |
| 4,850,873 A | 7/1989 | Lazzara et al. |
| 5,195,891 A | 3/1993 | Sulc |
| 5,636,989 A | 6/1997 | Somborac et al. |
| 5,685,714 A | 11/1997 | Beaty et al. |

(Continued)

FOREIGN PATENT DOCUMENTS

| | | |
|---|---|---|
| DE | 10333013 | 2/2005 |
| EP | 2263600 | 12/2010 |

(Continued)

*Primary Examiner* — Heidi M Eide
*Assistant Examiner* — Mirayda A Aponte
(74) *Attorney, Agent, or Firm* — Knobbe Martens Olson & Bear LLP

(57) ABSTRACT

The present application relates to a fitting for insertion into a dental implant in an insertion orientation defining a central insertion axis. The fitting includes at least one resilient spring member which extends from a body portion. It further includes an alignment feature for aligning the fitting relative to the dental implant about the insertion axis. The alignment feature extends distally beyond the distal end of the spring member.

17 Claims, 5 Drawing Sheets

(56) References Cited

U.S. PATENT DOCUMENTS

| | | | |
|---|---|---|---|
| 5,725,375 A | 3/1998 | Rogers | |
| 5,782,918 A | 7/1998 | Klardie et al. | |
| 5,829,977 A | 11/1998 | Rogers et al. | |
| 5,865,622 A | 2/1999 | Aleksey | |
| 5,873,722 A | 2/1999 | Lazzara et al. | |
| 5,989,026 A | 11/1999 | Rogers et al. | |
| 5,989,028 A | 11/1999 | Niznick | |
| 6,012,923 A | 1/2000 | Bassett et al. | |
| 6,030,219 A | 2/2000 | Zuest et al. | |
| 6,068,479 A | 5/2000 | Kwan | |
| 6,193,516 B1 | 2/2001 | Story | |
| 6,217,331 B1 | 4/2001 | Rogers et al. | |
| 6,290,500 B1 | 9/2001 | Morgan et al. | |
| 6,299,447 B1 | 10/2001 | Zuest et al. | |
| 6,332,777 B1 * | 12/2001 | Sutter | A61C 8/0001 433/173 |
| 6,382,977 B1 | 5/2002 | Kumar | |
| 6,488,501 B1 | 12/2002 | Harding | |
| 6,590,654 B1 | 7/2003 | Sirat et al. | |
| 6,592,370 B2 | 7/2003 | Morgan | |
| 6,644,969 B2 | 11/2003 | Kumar | |
| 6,648,643 B2 | 11/2003 | Hollander et al. | |
| 6,733,292 B2 | 5/2004 | Odrich et al. | |
| 6,981,871 B2 | 1/2006 | Mullaly et al. | |
| 6,991,462 B2 | 1/2006 | Morgan | |
| 7,104,797 B2 | 9/2006 | Rassoli | |
| 7,114,952 B2 | 10/2006 | Morgan | |
| 7,338,286 B2 | 3/2008 | Porter et al. | |
| 7,344,376 B2 | 3/2008 | Beaty et al. | |
| 7,484,959 B2 | 2/2009 | Porter et al. | |
| 7,632,095 B2 | 12/2009 | Ostman et al. | |
| 7,780,446 B2 | 8/2010 | Sanchez et al. | |
| 8,002,547 B2 | 8/2011 | Porter et al. | |
| 8,033,826 B2 | 10/2011 | Towse et al. | |
| 8,070,491 B2 | 12/2011 | Mundwiler et al. | |
| 8,113,835 B2 | 2/2012 | Yau et al. | |
| 8,187,000 B2 | 5/2012 | Schaub | |
| 8,747,112 B2 | 6/2014 | Brun | |
| 8,753,118 B2 | 6/2014 | Randall | |
| 8,888,486 B2 | 11/2014 | Goodman et al. | |
| 8,944,816 B2 | 2/2015 | Robb et al. | |
| 8,944,817 B2 | 2/2015 | Fischler et al. | |
| 8,944,818 B2 | 2/2015 | Robb et al. | |
| 9,033,709 B1 | 5/2015 | Allen et al. | |
| 9,095,398 B2 | 8/2015 | Courvoisier et al. | |
| 2004/0038179 A1 | 2/2004 | Kumar et al. | |
| 2004/0101806 A1 | 5/2004 | Kumar et al. | |
| 2004/0101808 A1 | 5/2004 | Porter et al. | |
| 2007/0059666 A1 | 3/2007 | Zickman et al. | |
| 2008/0261174 A1 | 10/2008 | Gittleman | |
| 2008/0293013 A1 | 11/2008 | Lussi et al. | |
| 2009/0111072 A1 | 4/2009 | Lombardo et al. | |
| 2009/0130629 A1 | 5/2009 | Towse et al. | |
| 2009/0136899 A1 | 5/2009 | Porter et al. | |
| 2009/0298013 A1 | 12/2009 | Baruc | |
| 2010/0055645 A1 | 3/2010 | Mullaly et al. | |
| 2010/0159421 A1 | 6/2010 | Koka et al. | |
| 2010/0184002 A1 | 7/2010 | Ranck et al. | |
| 2010/0209877 A1 | 8/2010 | Hogan et al. | |
| 2010/0216092 A1 | 8/2010 | Garcia Saban et al. | |
| 2010/0248184 A1 | 9/2010 | Soler et al. | |
| 2011/0014588 A1 | 1/2011 | Seavey et al. | |
| 2011/0076644 A1 | 3/2011 | Engman | |
| 2011/0244425 A1 | 10/2011 | Wiener | |
| 2011/0318710 A1 | 12/2011 | Towse et al. | |
| 2012/0003606 A1 | 1/2012 | Fischler et al. | |
| 2012/0052463 A1 | 3/2012 | Pollet | |
| 2012/0058448 A1 | 3/2012 | Ang | |
| 2013/0004915 A1 | 1/2013 | Bellanca et al. | |
| 2013/0101960 A1 | 4/2013 | Fischler et al. | |
| 2013/0171584 A1 | 7/2013 | Brun | |
| 2014/0030676 A1 | 1/2014 | Di Girolamo et al. | |
| 2014/0099600 A1 | 4/2014 | Harrison | |
| 2014/0242545 A1 | 8/2014 | Brun | |
| 2015/0044638 A1 | 2/2015 | Baez | |
| 2015/0118651 A1 | 4/2015 | Richard | |
| 2015/0140512 A1 | 5/2015 | Bachler et al. | |
| 2015/0147724 A1 | 5/2015 | Staudenmann et al. | |

FOREIGN PATENT DOCUMENTS

| | | |
|---|---|---|
| EP | 1 419 746 B1 | 6/2011 |
| EP | 2752168 | 7/2014 |
| EP | 2803331 | 11/2014 |
| KR | 2007102641 | 10/2007 |
| KR | 101401793 | 5/2014 |
| WO | WO 93/20773 | 10/1993 |
| WO | WO 2001/066033 | 9/2001 |
| WO | WO 2010/093737 | 8/2010 |
| WO | WO 2011/132007 | 10/2011 |
| WO | WO 2013/186764 | 12/2013 |
| WO | WO 2013/186765 | 12/2013 |
| WO | WO 2014/064117 | 5/2014 |
| WO | WO 2014/068561 | 5/2014 |
| WO | WO 2014/095033 | 6/2014 |
| WO | WO 2014/095034 | 6/2014 |
| WO | WO 2014/153487 | 9/2014 |

* cited by examiner

ABUTMENT POSITION LOCATOR

PRIORITY INFORMATION

This application is a continuation of U.S. application Ser. No. 14/271,268 filed May 6, 2014, titled ABUTMENT POSITION LOCATOR, which is a continuation of U.S. application Ser. No. 13/341,328 filed Dec. 30, 2011, titled ABUTMENT POSITION LOCATOR, now issued as U.S. Pat. No. 8,747,112, the entirety of each application is hereby incorporated by reference.

BACKGROUND OF THE INVENTION

Field of the Invention

The present disclosure pertains in general to the field of oral, dental or maxillofacial restorative medical procedures, and products related thereto. More particularly the present disclosure relates to devices and methods for facilitating determination of a position and orientation of components, like implants, involved in such procedures.

Description of the Related Art

A common fitting, also referred to as an abutment position locator, includes a friction fit connection. FIG. 4 shows an example of such a common fitting 100. The fitting 100 comprises an insertion portion 102 at a distal end of the fitting 100. This portion 102 has several springs 104 projecting in the insertion direction. These springs 104 are expandable perpendicularly to the insertion axis of the fitting 100, for impeding a movement of the fitting 100 relative to the dental implant along the insertion axis when inserted into the dental implant.

In order to achieve this, the dental implant is configured such that the springs 104 are expanded radially inwardly towards the central insertion axis of the fitting 100 upon insertion of the fitting 100 into the implant and, hence, frictionally engage the dental implant due to their constant pressure exerted on the implant. In some embodiments of the prior art, the dental implant comprises a groove or recesses into which projections on the springs 104 can engage in order to increase the impeding force against a movement of the fitting relative to the dental implant.

Further, the springs 104 are arranged in a manner such that the fitting 100 only fits into the dental implant in a certain alignment so that the springs 104, at the same time, form an alignment feature for rotationally aligning the fitting relative to the dental implant about the insertion axis. In other words, the fitting 100 cannot be inserted into the dental implant in a misaligned rotational position relative to the dental implant so that the arrangement of the springs 104 ensures a correct alignment of the fitting in the dental implant.

US 2009/0130629 A1, which is hereby incorporated by reference in its entirety, discloses a two-piece dental abutment system having similar springs projecting distally to be inserted into a dental implant. EP 1 419 746 A2, which is hereby incorporated by reference in its entirety, similarly discloses a dental implant system in which a separate abutment is not provided but the dental prosthesis itself is provided with respective fitting features such as resilient spring members and an alignment feature.

A problem with the prior art constructions disclosed above is that the fitting features lose their functionality if inserted in a misaligned position relative to the dental implant. With the prior art constructions, it easily happens that one or several of the springs 104 are plastically deformed upon insertion into the dental implant and the friction force to be provided by the springs is severely decreased or lost completely. As a consequence, the fitting does not work properly, if it was not inserted in the correct way.

Various optical scanning methods are known in the art, such as the method and apparatus disclosed in U.S. Pat. No. 6,590,654, which is incorporated herein by reference in its entirety for all purposes.

SUMMARY OF THE INVENTION

It is an object of certain embodiments to further develop the fittings of the prior art such that an insertion of the fitting in a wrong alignment is prevented. An object, therefore, of certain embodiments is to further develop the fittings of the prior art such that the fitting can be used easily without the risk of a decrease in the friction force due to a wrong insertion into a dental implant. At the same time, the functions of the prior art fittings of impeding a movement of the fitting relative to the dental implant along the insertion axis and of ensuring of a correct alignment relative to the dental implant are to be provided by the further developed construction.

This object is achieved by a fitting according to claim 1, an abutment according to claim 17, a dental prosthesis according to claim 18 and a dental implant system according to one of claims 19 and 20. Further advantageous aspects and features of the certain embodiments are defined in the dependent claims.

According to some embodiments, a fitting for insertion into a dental implant in an insertion orientation defining a central insertion axis and an insertion direction of the fitting comprises at least one resilient spring member being expandable/compressible perpendicularly to the insertion axis of the fitting which is suitable for impeding a movement of the fitting relative to the dental implant along the insertion axis when inserted into the dental implant and an alignment feature for rotationally aligning the fitting relative to the dental implant about the insertion axis. The fitting is characterized in that the alignment feature extends further in the insertion direction than the spring member.

In other words, in some embodiments, the alignment feature extends further distally than the spring member, when the insertion direction is the distal direction of the fitting. In this regard, the portion of the fitting to be inserted into the dental implant is defined as the distal portion of the fitting, whereas the opposite portion of the fitting is defined as the proximal portion of the fitting. Accordingly, the distal direction is the insertion direction of the fitting, namely the direction in which the fitting is to be inserted into the dental implant, when the fitting is correctly oriented with respect to the dental implant.

Preferably, in some embodiments, the at least one spring member is a resilient finger extending parallel to the insertion axis of the fitting. This configuration of the spring member is easy to manufacture and works effectively in impeding the movement of the fitting relative to the dental implant, when inserted into the dental implant.

Particularly, in some embodiments, the at least one spring member is provided with a projection which is configured to engage into a groove or recess in the dental implant so that the movement impeding force of the spring member with respect to the dental implant is further increased.

In a one embodiment, the fitting comprises a plurality of spring members. The plurality of spring members enhances the efficiency of impeding a movement of the fitting relative to the dental implant and, at the same time, simplifies the insertion into the dental implant.

In a further embodiment, the plurality of spring members is symmetrically arranged around the insertion axis. Being symmetrically arranged means in this context that the arrangement of the spring members is symmetric with respect to a point in the center of the plurality of spring members. Being symmetrically arranged can also mean that the spring member are rotationally symmetric or having reflection symmetry. A symmetrical arrangement of the spring members provides for a better performance of the fitting. However, it is also possible to arrange the at least one spring member or the plurality of spring members in an asymmetric arrangement.

A further arrangement of the spring members around the insertion axis, such that an angular distance with respect to the insertion axis between two adjacent spring members of the plurality is the same for all spring members of the plurality, also provides for better results in fixing the fitting with respect to the dental implant. In other words, it is advantageous for the spring members to be arranged equally spaced peripherally around the insertion axis, being a central axis of the fitting.

The alignment feature can comprise a recess in a peripheral portion of it in which one of the at least one spring member(s) is disposed. The recess can also be provided as an opening in the alignment feature in the peripheral portion of it.

This means that the alignment feature extending distally beyond the spring member is formed such that the spring member or the plurality of spring members is disposed in a peripheral portion of the alignment feature in a recess so that the spring member is expandable perpendicularly to the insertion axis independently from the alignment feature. By this construction, it is easily possible to provide an alignment feature which independently extends further in the insertion direction than the spring member(s) and safely avoids any misalignment of the fitting with respect to the dental implant. At the same time, the alignment feature allows for the at least one spring element to be expandable/compressible perpendicularly to the insertion direction in order to impede a movement of the fitting relative to the dental implant by frictionally engaging the dental implant.

Each of the at least one spring member(s) can be disposed in one respective recess. In other words, if the fitting comprises a plurality of spring members, each one is disposed in a respective recess so that one recess houses one spring member. This preferred embodiment allows for a particular robust configuration of the alignment feature and the spring members.

The alignment feature can comprise a plurality of rods extending in parallel to the insertion axis and being circumferentially distributed about the insertion axis. In this regard, at least two adjacent rods of the plurality can be connected to each other at an axial position further in the insertion direction than the axial position of the at least one spring member. In other words, at least two adjacent rods are connected to each other distally with respect to the at least one spring member. Thus, the alignment feature (partially) surrounds the respective spring element so that the spring element cannot be plastically deformed upon a wrong insertion into the dental implant.

Each of the plurality of rods can be connected to the adjacent two rods at an axial position further in the insertion direction than the axial position of the at least one spring member. This further improves the effect of only two connected adjacent rods. In one arrangement, the rods of the alignment feature and the fingers of the spring members are alternately arranged around the central insertion axis and the rods of the alignment feature are connected to each adjacent rod such that each of the fingers of the spring elements is (partially) surrounded by two rods and a connection between the two rods.

In some embodiments, the fitting further comprises a conical seating surface at an axial position less far in the insertion direction than the axial position of the at least one spring member. In other words, the conical seating surface is provided proximally, preferably directly proximally, from the at least one spring member. Such a conical seating surface improves the stability of the fitting on the implant and makes it less sensitive to external influences such as being touched by mistake.

The fitting can be made of a metallic material, for example alloyed titanium or, alternatively, of a polymeric material such as polyether-ether-ketone (PEEK).

Further advantageous features and aspects of the invention become apparent from the claims and description of the preferred embodiments below. For purposes of summarizing certain embodiments and the advantages achieved over the prior art, certain objects and advantages have been described above. It is to be understood that not necessarily all such objects or advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

BRIEF DESCRIPTION OF THE DRAWINGS

These and other features, aspects and advantages of the present disclosure will now be described in connection with non-exclusive embodiments, in reference to the accompanying drawings. The illustrated embodiments, however, are merely examples and are not intended to limit the invention. The following are brief descriptions of the drawings, which may not be drawn to scale.

DETAILED DESCRIPTION OF THE PREFERRED EMBODIMENTS

This disclosure sets forth various embodiments that relate to position locators affixable to said components in a defined relationship, having at least one surface detectable by optical scanning for the position and orientation determination.

For example, some embodiment relate to a fitting for insertion into a dental implant in an insertion orientation defining a central insertion axis and an insertion direction of the fitting. The fitting cam comprise at least one resilient spring member being expandable perpendicularly to the insertion axis of the fitting, for impeding a movement of the fitting relative to the dental implant along the insertion axis when inserted into the dental implant, and an alignment feature for rotationally aligning the fitting relative to the dental implant about the insertion axis.

In some embodiments, a dental implant system comprises a dental implant for installation in the bone and an abutment or a dental prosthesis to be introduced into the dental implant. The dental implant comprises a proximal end being located near an exterior surface of the bone and an interior bore extending distally from the proximal end, the interior bore being configured for an introduction of the abutment or the prosthesis. The abutment or prosthesis comprises a fitting for distally insertion into the dental implant in an insertion orientation defining a central insertion axis of the abutment or dental prosthesis. The fitting comprises at least one resilient spring member being expandable perpendicularly to the insertion axis for impeding a movement of the abutment or dental prosthesis relative to the dental implant along the insertion axis when inserted into the dental implant and an alignment feature for rotationally aligning the abutment or dental prosthesis relative to the dental implant about the insertion axis.

Figure 1:
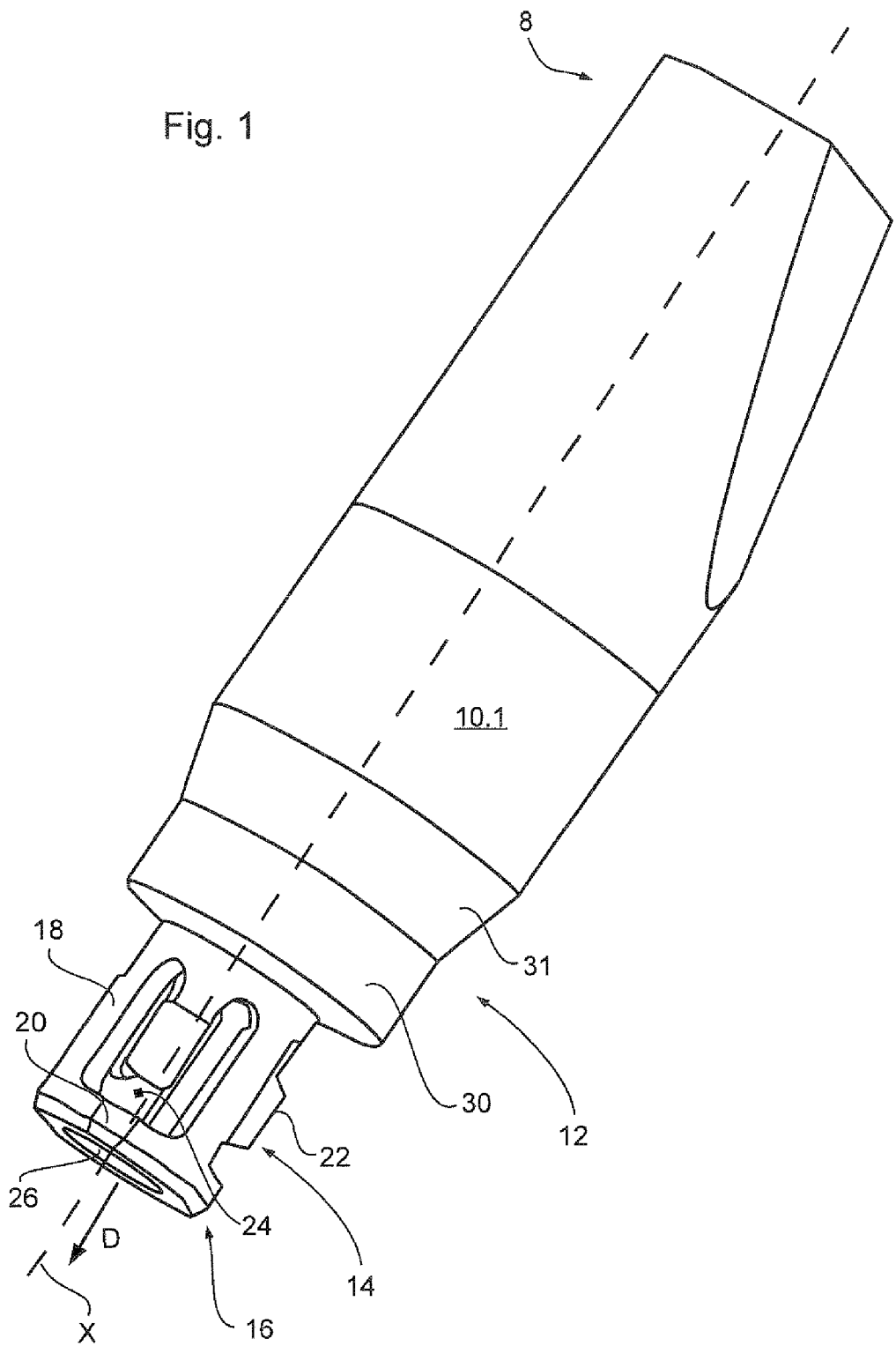
FIG. 1 illustrates an abutment having a fitting for insertion into a dental implant according to a first embodiment.

With reference now to the illustrated embodiments, FIG. 1 shows a first exemplary embodiment of an abutment 8 having a fitting 10.1 of according to one configuration. The fitting 10.1 is provided at a distal portion 12 of the abutment 8 and comprises a plurality of resilient fingers 14 working as spring elements. If the fitting 10.1 is partially inserted into a dental implant, the resilient fingers 14 are radially expanded/compressed inwardly and frictionally engage the dental implant in order to impede a movement of the fitting 10.1 relative to the dental implant (not shown). The fitting 10.1 has a central insertion axis X and defines an insertion direction D in which the fitting 10.1 and hence the abutment 8 is to be inserted into the dental implant.

The resilient fingers 14 are mainly for impeding a movement of the abutment with respect to this insertion axis X. Each of the resilient fingers 14 comprises a projection 22 which projects radially outwardly from the central insertion axis X of the fitting 10.1 and is configured for engaging into a groove or a recess in the dental implant in order to increase the frictional force of the fitting 10.1 with respect to the dental implant.

Between respective adjacent resilient fingers 14 of the fitting 10.1, a rod 18 is provided which extends distally beyond the resilient fingers 14. In other words, the rods 18 extend further in the insertion direction D than the resilient fingers 14. Adjacent rods 18 are respectively connected with a connection 20 distally to the resilient fingers 14 so that each of the resilient fingers 14 is surrounded by adjacent rods 18 and a connection 20 of the rods 18. The rods 18 and the connections 20 are configured to form an alignment feature 16 in that they are formed in a specific geometric way so that the fitting 10.1 only fits into the dental implant in a certain orientation and alignment.

Accordingly, trying to insert the fitting 10.1 into the dental implant in a misaligned state will not work so that the operator must rotate the fitting 10.1 around the insertion axis X in order to find the correct orientation and alignment of the fitting 10.1 with respect to the dental implant.

The connections 20 connecting respective adjacent rods 18 of the alignment feature are arranged circumferentially around the central insertion axis X and form a substantially circular opening 26 at a distal portion of the alignment feature 16. On the other hand, the resilient fingers 14 are provided in a peripheral portion of the alignment feature 16 and can be elastically deformed independently from the alignment feature 16 which is not provided to be elastically deformed. Each one of the resilient fingers 14 is disposed in a respective recess 24, which is formed as an opening, in a peripheral portion of the alignment feature 16 and provides for an independent elastic deformation of the resilient fingers 14, while the inelastic alignment feature 16 prevents the resilient fingers from being plastically deformed unintentionally upon insertion into the dental implant.

Further, the fitting comprises a cylindrical shoulder 30 and a conical seating surface 31 proximal to the shoulder 30.

Figure 2:
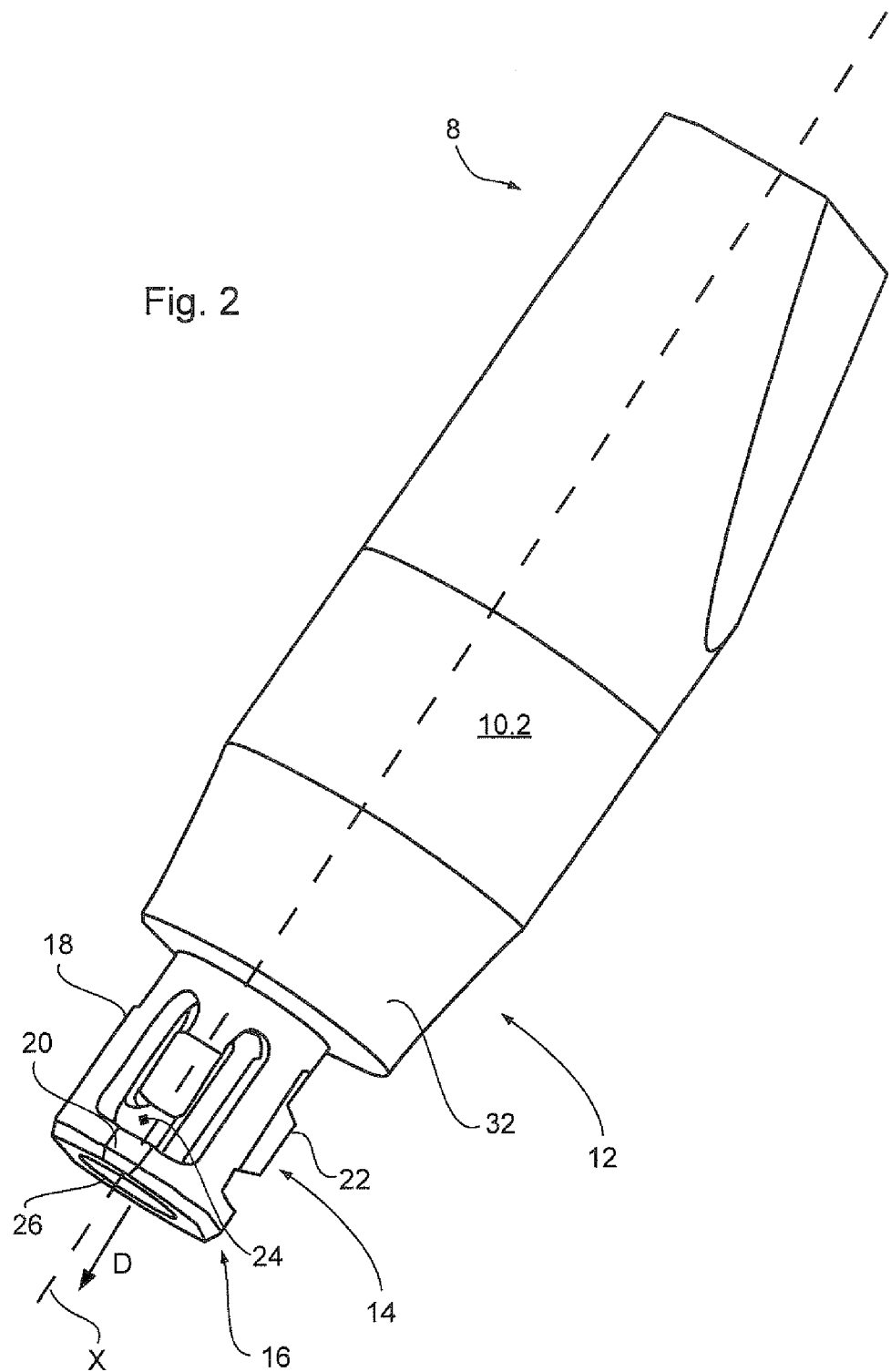
FIG. 2 illustrates an abutment having a fitting for insertion into a dental implant according to a second embodiment.

FIG. 2 shows an modified embodiment of a fitting 10.2 for an abutment 8. The same elements in FIG. 2 and FIG. 1 are assigned the same reference numbers and are not repeatedly described.

Figure 5:
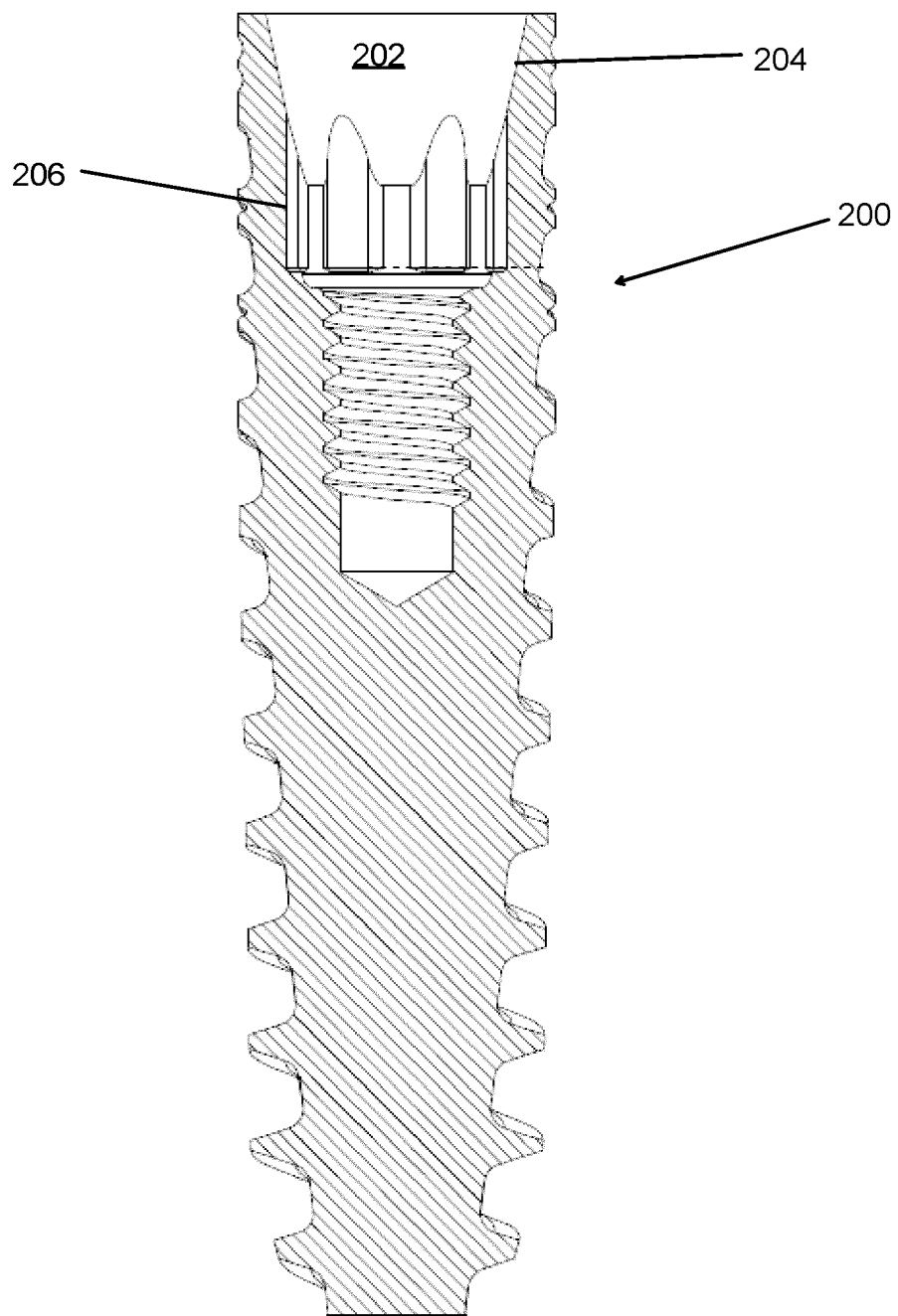
FIG. 5 is a cross-sectional longitudinal view of an example of a dental implant that can be used in combination with a fitting according to one embodiment.

In contrast to the embodiment according to FIG. 1, a conical seating surface 32 of the fitting 10.2 is provided at a position directly proximal to the resilient fingers 14 and the rods 18. This conical surface improves the stability of the fitting on the dental implant and makes it less sensitive to external influences. FIG. 5 illustrates a longitudinal cross-section of one example of a dental implant 200 that can be used with the fitting 10.2 and abutment 8 of FIG. 2. The implant 200 can include an internal cavity 202, which can include a conical portion 204 for engaging the conical seating surface 32 of the fitting 10.2. The internal cavity 202 can also include an alignment portion 206 for engaging the alignment feature 16 of the fitting 10.2 as described above.

Both embodiments according to FIGS. 1 and 2 comprise three resilient fingers 14 and three rods 18 between the resilient fingers 14. The connections 20 between each two adjacent rods 18 are thus also provided three-fold in these preferred embodiments. The resilient fingers 14 are symmetrically arranged, wherein one spring is arranged per 120° of angular distance with respect to the central insertion axis X. Naturally, it is also possible to provide more or less spring elements being arranged symmetrically or asymmetrically. The same applies for the rods 18 which are also arranged symmetrically wherein one rod 18 is provided per 120° angular distance in-between adjacent fingers 14.

Figure 3:
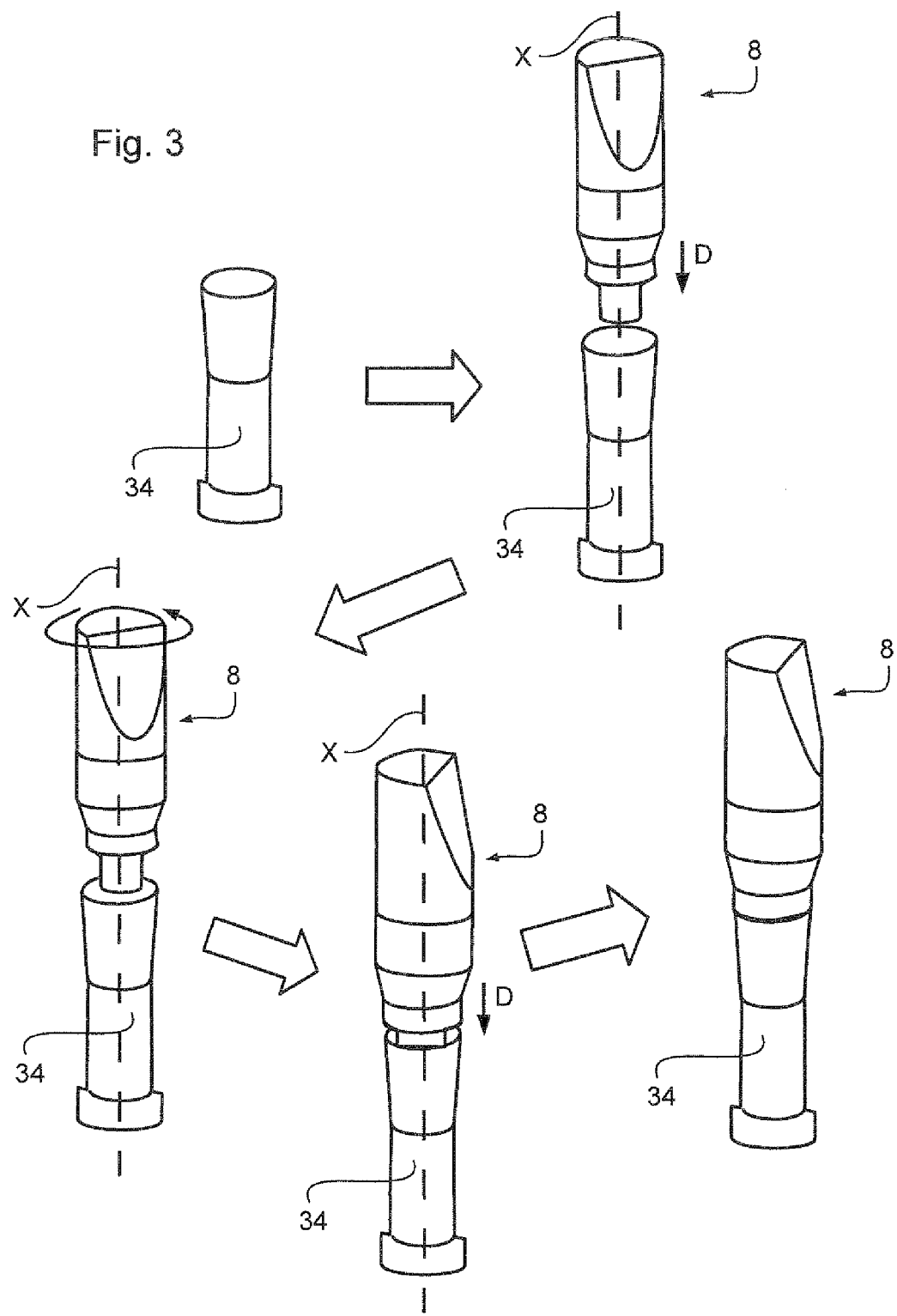
FIG. 3 illustrates the process of inserting a fitting of an abutment into a dental implant.
Figure 4:
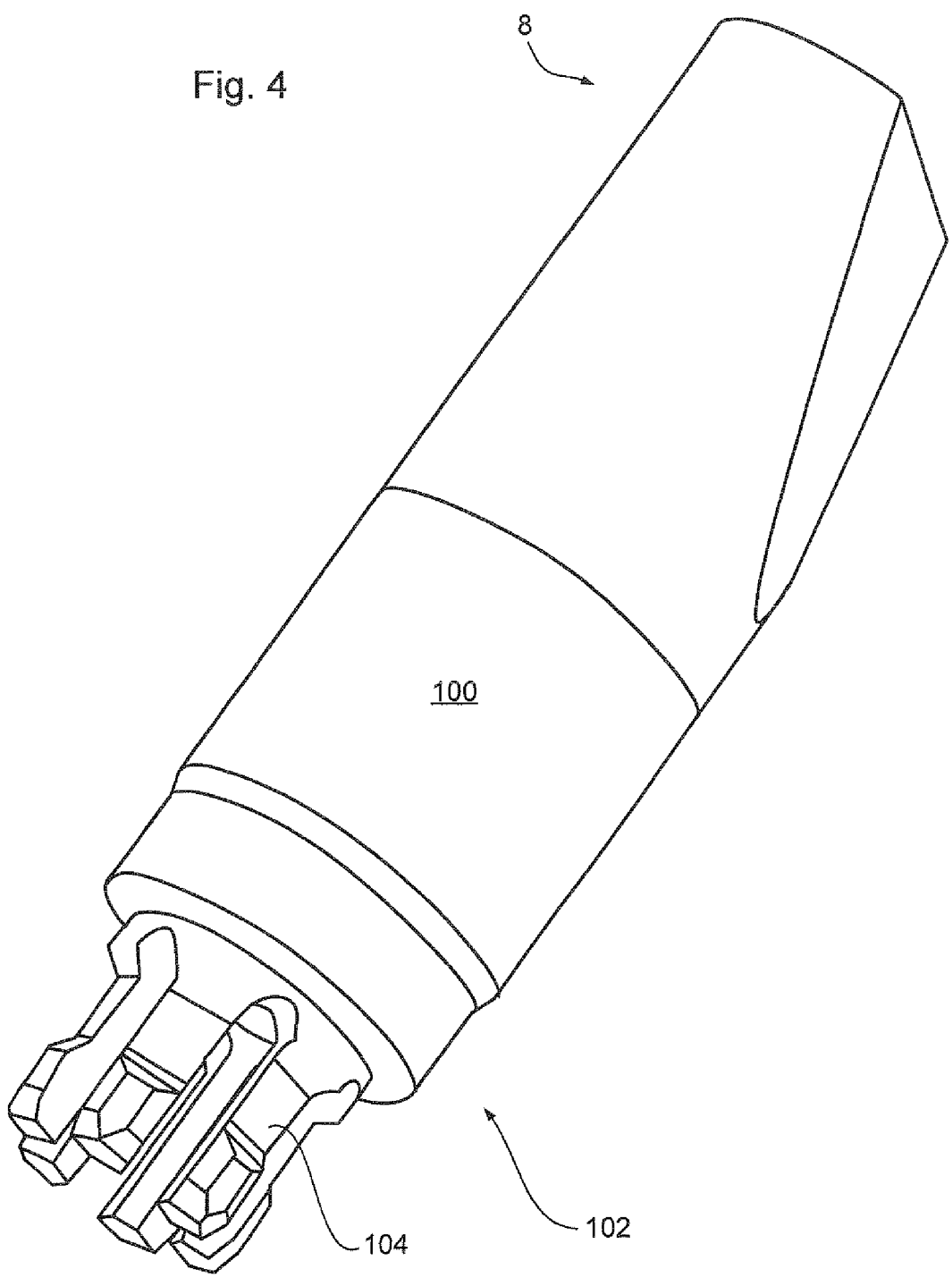
FIG. 4 illustrates an abutment having a fitting of the prior art.

FIG. 3 illustrates the process of introducing the fitting of an abutment 8 into a dental implant 34. At first, the abutment 8 is moved to contact the dental implant 34. Since the alignment of the abutment 8 with respect to the dental implant 34 might at first not be correct, the abutment 8 is rotated about the insertion axis X until the abutment is properly aligned with respect to the dental implant 34. Once the correct alignment of the abutment 8 with respect to the dental implant 34 is reached, the abutment 8 can be further inserted into the dental implant 34 and the spring members can frictionally engage the dental implant 34 in order to impede a movement of the fitting and thus the abutment 8 with respect to the dental implant 34 along the insertion axis X.

The above description of the preferred embodiments refers to a respective abutment 8. However, the fitting 10.1, 10.2 is also applicable to a dental prosthesis directly without a separate abutment between the dental implant and the prosthesis. In addition, the abutment 8 with a fitting as described above can be modified to comprise various types of dental components, such as, for example, an impression coping or feather, a position locator, a healing cap or abutment, a temporary abutment or temporary restoration/prosthetic.

Using a fitting according to the above described embodiments, it is not so easy to plastically deform the spring elements by mistake upon inserting the fitting into the dental implant because the alignment feature avoids axial forces to act on the spring members. Accordingly, these embodiments provide for a fitting for an abutment or a dental prosthesis which can be used safely and with a considerably lower risk of plastically deforming spring elements to be used for fixing the abutment or the dental prosthesis in the dental implant.

It is clear that the meaning of dental implant in the context of the present application encompasses a model (e.g., a computer simulation) of or an implant replica.

Examples of Use of Position Locators

In an initial point of the method, an implant is provided implanted in bone tissue of a patient. After a healing and osseointegration period a component, such as a dental restoration, like a single tooth, a bridge, or other framework, have to be produced and affixed to the implant at a connection interface thereof. For this purpose, the exact position and orientation of the implant have to be determined. To this end, an impression of the dental situation is taken.

The position and orientation of an implant or an abutment in a model, or an impression coping in an impression has to be determined with high precision by optical scanning methods. The impression is a negative of at least a portion of the oral cavity of a patient. The impression is made of a jaw portion comprising an already implanted dental implant. The implant has been implanted previously in the jaw bone tissue, and was optionally left in place for healing and osseointegration with the jaw bone tissue for a solid fixation therein. Thus the dental implant provides an anchored platform having a defined connection interface for fixation of dental restorations to the jaw bone. Dental restorations comprise dental bridges, single tooth restorations, etc. The dental restorations may be directly fixated to the dental implant or intermediate components like abutments may be used.

From the impression, data will be derived for the position and orientation of the dental implant. A plurality of dental implants may be present. As the implants are anchored in jaw bone tissue, only a top portion of the connection interface or abutment protruding into the oral cavity would be present in impressions. In order to provide improved orientation data for the longitudinal axis of the dental implant, impression copings and position locators are used during impression taking and subsequent scanning of the impression or a model prepared from the impression, respectively. This will now be explained in more detail. The impression is taken from the patient with impression copings, which are attached to the dental implant(s). The impression copings thus leave a negative impression in the impression, or are left in the impression when the impression material has solidified. The impression is then removed from the patient. As the impression copings are fixated to the dental implants, these are provided with a smooth surface such that they easily loosen from the solidified impression material. The impression copings are removed from the dental implants. The impression and the impression copings are then available for further processing steps towards producing a dental restoration.

An implant replica or an abutment replica is attached to the impression coping in the next step. This assembly is repositioned in the impression into the corresponding recess in the impression in a following step. In this manner, the implant replica or the abutment replica protrudes from the impression at the exact position and in the precise orientation relative to the registered anatomical situation of the patient from which the impression was taken.

The position locator may also be used for intra oral scanning, wherein the position locator is attached directly to the implant in the oral cavity of the patient. In particular, the intra oral scanning is an optical scanning. The optical scanning is performed by means of an intra oral optical scanner.

A model is then cast from the impression. When the model is solidified, it is removed from the impression, together with the impression coping. This model corresponds with high precision to the anatomical situation of the patient. Implant replica in the model are precisely positioned at correct positions and with correct orientation in the model. The impression coping are then threadably removed from the fixated implant replica or abutment replica. As impression coping have a smooth surface these are not suited for optical scanning.

From the model, a dental restoration model, such as a bridge framework model is prepared, manually taking into consideration aesthetical, geometrical, and mechanical requirements. The bridge framework model may for instance be an acrylic framework prepared by using non-engaging temporary abutments or cylinders. The acrylic framework may then be manually reduced to a desired shape. Subsequently, the model and the dental restoration model are scanned with an optical scanner to provide patient data and data for the dental restoration in steps respectively. The patient data and data for the dental restoration are subsequently matched and provided in a virtual computer based environment in step for planning the final restoration in step. Merging of the patient data and data for the dental restoration is facilitated thanks to the use of the improved position locators providing data with higher precision and resolution. When virtual planning is finished, production data is provided in a step for manufacturing of a dental restoration, such as a bridge framework, to be installed in the patient.

Prior to scanning, the position locators are affixed to the implant replica or abutment replica. The position locators are now arranged in a precise relationship to the implant replica or abutment replica, corresponding to the anatomical situation of the patient. By detecting the position and orientation of the position locators from optical scan data, the exact position of the implant replica or abutment replica is determinable. This is very important for being able to provide high precision production data and finally dental restorations based on this production data.

Prior to scanning, position locators are also threadably affixed to the dental restoration model. These position locators provide, when scanned in an optical scanner, exact data for the position of a connection interface mating with a connection interface of the replica implants or replica abutments. A plurality of dental implants or abutments may be present. In this case, one position locator will be used for every dental implant.

From optical scanning, the model and the dental restoration model are digitized to provide corresponding data. A calculation is made where the implants or copings are located. As the position locators provide high precision data from optical scanning, this is facilitated by the position locators. For instance, the conical portion of the frusto conical portion is used for calculation of the longitudinal center axis of a position locator. The top surface of the frusto conical portion of the position locator is used to determine the position in space of the position locator. In this manner, a vector for the position and orientation of the position locator is determined. As the longitudinal axis of the position locator and the dental implant or abutment coincide or have a defined relationship, the orientation of the dental implant or abutment is determinable with high precision. As the top portion is provided with high precision and has a defined relation to the connection interface, also the exact position of the dental implant or abutment is determinable.

Also, the dental restoration model having position locator affixed thereto provides data for the position of the connection interface mating with the connection interface of the dental implants or abutments with high precision. Position locators for the dental restoration model, may differ from position locators for implants or abutments with regard to the connection interface. The connection interfaces of the dental restoration model and the implants or abutments are mating male/female connection interfaces. The connection interfaces themselves differ in dependence of the specific implant system used.

The patient data and data for the dental restoration are subsequently matched and provided in a virtual computer based environment for planning the final restoration. When virtual planning is finished, production data is provided for manufacturing of a dental restoration, such as a bridge framework, to be installed in the patient. Further adaptation of the manufactured product, e.g. veneering may be performed manually before finally installing the dental restoration in the patient. Installation is performed smoothly as the dental restoration perfectly fits to the dental implants already installed in the patient.

Although the inventions have been disclosed in the context of a preferred embodiments and examples, it will be understood by those skilled in the art that the present disclosure extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It can be also contemplated that various combinations or subcombinations of the specific features and aspects of the embodiments can be made and still fall within the scope of the invention. Accordingly, it should be understood that various features and aspects of the disclosed embodiments can be combine with or substituted for one another in order to form varying modes of the disclosed invention. Thus, it can be intended that the scope of the present disclosure herein disclosed should not be limited by the particular disclosed embodiments described above.

What is claimed is:

1. Fitting for insertion into a dental implant in an insertion orientation defining a central insertion axis, comprising:
   a body portion extending along a central axis;
   at least one resilient spring member extending distally from a distal end of the body portion; and
   an alignment feature extending distally from the distal end of the body portion, the alignment feature configured to align the fitting relative to the dental implant about the insertion axis,
   wherein the alignment feature is positioned distally beyond a distal end of the at least one resilient spring member,
   wherein the alignment feature comprises a closed structure and at least one opening formed in the closed structure,
   wherein one of the at least one spring member is disposed in the at least one opening of the alignment feature,
   wherein the opening is a through hole on a peripheral portion of the alignment feature such that an axis passing through the opening is substantially perpendicular to the central axis.

2. The fitting of claim 1, wherein the closed structure comprises a circumferentially closed structure.

3. The fitting of claim 1, wherein the at least one resilient spring member is configured to expand perpendicularly to the insertion axis.

4. The fitting of claim 3, wherein the at least one resilient spring member is configured to expand radially inward towards the insertion axis.

5. The fitting of claim 1, wherein the at least one spring member comprises a plurality of spring members.

6. The fitting of claim 5, wherein the plurality of spring members are symmetrically arranged around the insertion axis.

7. The fitting of claim 1, wherein each one of the at least one spring member is disposed in one respective opening.

8. The fitting of claim 1, wherein the alignment feature is configured to rotationally align the fitting relative to the dental implant about the insertion axis.

9. Fitting for insertion into a dental implant in an insertion orientation defining a central insertion axis, comprising:
   a body portion;
   at least one resilient spring member extending distally from a distal end of the body portion; and
   an alignment feature extending distally from the distal end of the body portion, the alignment feature configured to align the fitting relative to the dental implant about the insertion axis,
   wherein the alignment feature is positioned distally beyond a distal end of the at least one resilient spring member,
   wherein the alignment feature comprises a closed structure and at least one opening;
   wherein one of the at least one spring member is disposed in the at least one opening of the alignment feature; and
   wherein the closed structure comprises a plurality of rods and a plurality of connections coupled to adjacent rods.

10. Fitting for insertion into a dental implant in an insertion orientation defining a central insertion axis, comprising:
    a body portion;
    at least one resilient spring member extending distally from a distal end of the body portion; and
    an alignment feature extending distally from the distal end of the body portion, the alignment feature configured to align the fitting relative to the dental implant about the insertion axis,
    wherein the alignment feature is positioned distally beyond a distal end of the at least one resilient spring member, and
    wherein at least a portion of the alignment feature at an axial position distal the axial position of the at least one spring member has a radial dimension equal to that of the at least one resilient spring member.

11. An abutment comprising:
    a fitting for insertion into a dental implant in an insertion orientation defining a central insertion axis, the fitting comprising:
       at least one resilient spring member extending distally from a distal end of the abutment; and
       an inelastic alignment feature extending distally from the distal end of the abutment, the inelastic alignment feature configured to align the fitting relative to the dental implant about the insertion axis,
       wherein the inelastic alignment feature extends distally beyond a distal end of the at least one resilient spring member, wherein the inelastic alignment feature comprises a circumferentially closed structure and at least one opening formed in the circumferentially closed structure, the at least one opening being transverse to the central insertion axis, and wherein one of the at least one spring member is disposed in the at least one opening of the inelastic alignment feature.

12. The abutment of claim 11, wherein each one of the at least one spring member is disposed in one respective opening.

13. The abutment of claim 11, wherein the at least one resilient spring member is configured to expand perpendicularly to the insertion axis.

14. The abutment of claim 11, wherein the at least one spring member comprises a plurality of spring members.

15. The abutment of claim 14, wherein the plurality of spring members are symmetrically arranged around the insertion axis.

16. The abutment of claim 11, wherein the inelastic alignment feature is configured to rotationally align the fitting relative to the dental implant about the insertion axis.

17. An abutment comprising:

a fitting for insertion into a dental implant in an insertion orientation defining a central insertion axis, the fitting comprising:

at least one resilient spring member extending distally from a distal end of the abutment; and an inelastic alignment feature extending distally from the distal end of the abutment, the inelastic alignment feature configured to align the fitting relative to the dental implant about the insertion axis, wherein the inelastic alignment feature extends distally beyond a distal end of the at least one resilient spring member, and wherein at least a portion of the inelastic alignment feature at an axial position distal the axial position of the at least one spring member has a radial dimension equal to that of the at least one resilient spring member.

* * * * *